United States Patent [19]

Muffler et al.

[11] 4,343,742
[45] Aug. 10, 1982

[54] PROCESS FOR THE MANUFACTURE OF 2,3-PERFLUORO-1,4-DIOXANES AS WELL AS SOME SPECIAL REPRESENTATIVES OF COMPOUNDS OF THIS CLASS

[75] Inventors: Herbert Muffler, Frankfurt am Main; Günter Siegemund, Hofheim am Taunus; Werner Schwertfeger, Butzbach, all of Fed. Rep. of Germany

[73] Assignee: Hoechst Aktiengesellschaft, Frankfurt am Main

[21] Appl. No.: 225,150

[22] Filed: Jan. 14, 1981

Related U.S. Application Data

[63] Continuation-in-part of Ser. No. 167,404, Jul. 11, 1980, abandoned.

[30] Foreign Application Priority Data

Jul. 14, 1979 [DE] Fed. Rep. of Germany ....... 2928602

[51] Int. Cl.³ ............................................ C07D 319/12
[52] U.S. Cl. .................................. 549/380; 570/189; 424/278; 549/349
[58] Field of Search ....................................... 260/340.6

[56] References Cited

U.S. PATENT DOCUMENTS

| | | | |
|---|---|---|---|
| 3,475,456 | 10/1969 | Selman | 260/340.6 X |
| 3,578,684 | 5/1971 | Throckmorton | 260/340.2 |
| 3,883,559 | 5/1975 | Burdon et al. | 260/340.6 |
| 4,033,984 | 7/1977 | Martini | 260/340.6 |
| 4,067,884 | 1/1978 | Martini | 260/340.6 X |
| 4,118,399 | 10/1978 | Martini | 260/340.6 X |
| 4,136,121 | 1/1979 | Martini et al. | 260/340.6 X |
| 4,140,699 | 2/1979 | Martini | 260/340.6 |

FOREIGN PATENT DOCUMENTS 2648123 4/1978 Fed. Rep. of Germany .

OTHER PUBLICATIONS

C.A., 88, (1978), Eleev et al., 152514a.
J. of Fluorine Chemistry, 6, pp. 115–128 (1975) Coe et al.

*Primary Examiner*—Joseph Paul Brust
*Attorney, Agent, or Firm*—Curtis, Morris & Safford

[57] ABSTRACT

2,3-Perfluoro-1,4-dioxanes of the formula I

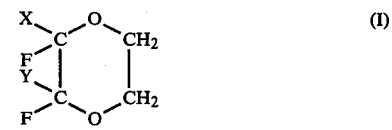

wherein X and Y independently from one another mean F or $CF_3$, are manufactured by reacting carbonyl compounds of the formula II

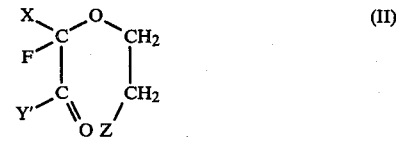

wherein
X has the same meaning as in formula I,
Y' has the same meaning as Y in formula I (F, $CF_3$), and additionally can be Cl and
Z=Cl, mesylate [$=OSO_2CH_3$] or tosylate=- [$OSO_2C_4H_6-CH_3$ (p)], with alkali metal fluorides and/or with ammonium fluoride. The reaction products I, among which those wherein at least one of both radicals X and Y is $CF_3$ are novel compounds, are solvents for highly fluorinated compounds and intermediates in various application fields.

6 Claims, No Drawings

PROCESS FOR THE MANUFACTURE OF 2,3-PERFLUORO-1,4-DIOXANES AS WELL AS SOME SPECIAL REPRESENTATIVES OF COMPOUNDS OF THIS CLASS

This application is a continuation in part of Ser. No. 167,404 filed July 11, 1980, now abandoned.

The simplest 2,3-perfluoro-1,4-dioxane is 2,2,3,3-tetrafluoro-1,4-dioxane. It is obtained, besides some other products, in the catalytic hydrogenation of perfluoro-1,4-dioxane-2[P. L. Coe et al., J. of Fluorine Chemistry 6, 115 to 128 (1975)]. It is isolated from the reaction mixture by distillation, with the ethoxydifluoroacetic acid methyl ester, which is also formed in the catalytic hydrogenation, likewise distilling over, followed by separation of the two compounds by reaction with sodium hydroxide solution (whereby only the ester is saponified). The 2,2,3,3-tetrafluoro-1,4-dioxane is obtained from the saponification mixture by extraction with ether and by the usual working up of the ether extract, in a yield of about 3%.

Because of the difficult obtention of 2,2,3,3-tetrafluoro-1,4-dioxane as well as due to the absolutely unsatisfactory yield, the object of the instant invention was to develop an improved process for the manufacture of this compound which, if possible, should also be suitable for the manufacture of further 2,3-perfluoro-1,4-dioxanes. It was not necessary, however, that the improved process to be developed could also be applied to the manufacture of 2,2,3,3-tetrakis-trifluoromethyl-1,4-dioxane, because the manufacture of the latter in practically quantitative yield from perfluoropinacole and 1,4-dioxane is already known [A. F. Eleev at al Izv. Nauk SSSR, Ser.Khim. 1978, 509].

The proposed object could be reached according to the invention by reacting certain carbonyl compounds with alkali metal fluorides and/or with ammonium fluoride.

A feature of the invention is, therefore, a process for the manufacture of 2,3-perfluoro-1,4-dioxanes of the general formula I

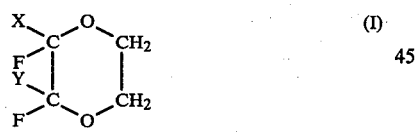

wherein X and Y, independently from one another, mean F or CF$_3$, which comprises reacting the carbonyl compounds of the general formula II

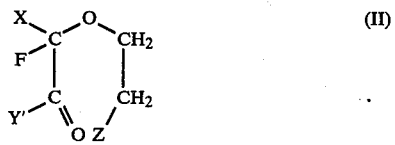

wherein
X has the same meaning as in formula I,
Y' has the same meaning as Y in formula I (F, CF$_3$) and additionally can also be Cl, and
Z=Cl, mesylate [=OSO$_2$CH$_3$] or tosylate [=OSO$_2$C$_4$H$_6$-CH$_3$(p)]
with alkali metal fluorides and/or with ammonium fluoride in an amount of at least about 1 mol of fluoride/mol of carbonyl compound II, if Y'=F or CF$_3$, or of at least about 2 mols of fluoride/mol of carbonyl compound II, if Y'=Cl.

The reaction can be illustrated by the following reaction scheme (a) if Y'=Y=F or CF$_3$:

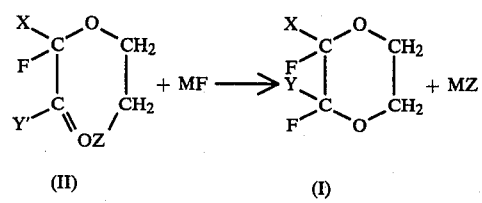

(b) if Y'=Cl:

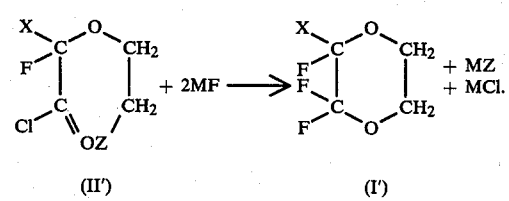

M in each case means an alkali metal or ammonium ion.

Formula II'=F Formula II with Y'=Cl,

Formula I'=Formula I with Y=F.

It was surprising that the radical Z in this reaction was not exchanged in the starting carbonyl compounds for F, which had to be expected at least at the beginning, but that there are formed the corresponding 2,3-perfluoro-1,4-dioxanes.

The starting compounds II for the process according to the invention are partially known (see, for example DE-OS 1,793,240). In part, they can be obtained using as starting compounds the known 2-ethoxy carboxylic acid esters III:

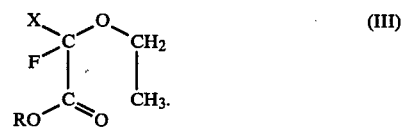

X in this case has the same meaning as in Formula II and R means alkyl.

The ester III can be converted into the sodium salts, for example, by saponification with NaOH, and these salts can subsequently be converted into acid chlorides with an inorganic acid chloride, such as POCl$_3$ or SOCl$_2$. The corresponding acid fluorides are obtained by reaction with inorganic fluorides, for example KF, from the acid chlorides. Light-catalyzed chlorination of these fluorides gives the 2-(β-chloroethoxy)-carboxylic acid fluorides IV:

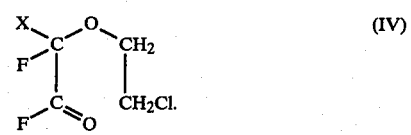

Compounds II, in which Z=Cl, are obtained in this case.

The compounds II with Z being mesyl or tosyl are advantageously manufactured in situ by reaction of the fluorocarbonyl compounds V:

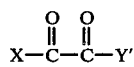  (V)

with the ethane derivatives VI:

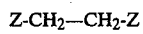  (VI),

X and Y' in formula having the same meaning as in formula II and Z, among the meanings mentioned above, being only mesyl or tosyl and with alkali metal fluorides and/or with ammonium fluoride.

The compounds V and VI are employed suitably in a molar ratio of about 1:1 to 1:1.5. When Y'=Y=F or $CF_3$, the amount of the fluoride used is at least about 1 mol per mol of V or VI. If Y'=Cl, the carbonyl compound II (with Y'=F) is obtained by using about 2 mols of fluoride. When using further amounts of fluoride there is performed the cyclization of the carbonyl compounds II yielding the corresponding 2,3-perfluorodioxane. An isolation of the compounds II is not necessary in this case.

Fluorides suitable for the process according to the invention are alkali metal fluorides and/or ammonium fluoride. Preferred fluorides are KF and/or CsF. The fluorides can be employed separately or in a mixture. Additives such as HF or so-called crown ethers (oxygen-containing macro cyclic compounds) can also be used.

For a successful reaction according to the invention, it is not necessary in principle to use more than about 1 or 2 mols of fluoride/mol of carbonyl compound II, but an excess of about 5 to 50 mols% is preferred. Higher excess does not provide any advantage.

Furthermore, the process is preferably carried out in an aprotic polar solvent. Suitable solvents are, for example: ethers, such as diethylene glycol dimethyl ether or tetraethylene glycol dimethyl ether; nitriles such as benzonitrile; acid amides such as dimethylformamide; sulfoxides such as dimethylsulfoxide; sulfolane; etc. The reaction temperature in general can be between about 20° and 200° C.; preferably it is between about 50° and 160° C., especially between about 60° and 130° C.

The reaction can be carried out at normal pressure or at elevated pressure.

The reaction time in general is between about 5 and 35 hours. For the reaction according to the invention it is practically without importance in which sequence the reaction components and the solvent are admixed. It is advantageous, however, to provide a homogeneous intermixing of the product by thoroughly stirring.

According to a preferred embodiment the fluoride is introduced into an aprotic polar solvent and reacted with the starting carbonyl compound II.

Subsequently, the mixture is heated. The resulting 2,3-perfluoro-1,4-dioxane is isolated from the reaction mixture by steam distillation.

If the carbonyl starting compound II is manufactured from a fluorocarbonyl compound V and an ethane derivative, it is advantageous to introduce the fluoride into an aprotic polar solvent, to add the fluorocarbonyl compound V under ice cooling and subsequently to react the mixture with the ethane derivative VI. After heating the mixture, the isolation of 2,3-perfluoro-1,4-dioxane is expediently carried out by steam distillation.

The 2,3-perfluoro-1,4-dioxanes of formula I, manufactured according to the invention, are colorless liquids which are resistant towards acid as well as towards basic hydrolysis. In organic solvents they are easily soluble with water, however, they are only slightly miscible.

The process allows the manufacture of 2,3-perfluoro-1,4-dioxanes in a relatively simple manner and with yields which, although not yet very good, are better than those obtained according to the known process of Coe et al. loc. cit. at least approximately by the factor 10; the yields in general are about 10 to 30% of the theory, in individual cases they can possibly amount to approximately 50%. Besides this, the 2,3-perfluoro-1,4-dioxanes of the formulae VII and VIII are novel compounds.

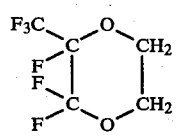   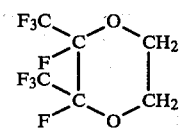

(VII)              (VIII)

The compounds produced by the process of this invention, including the 2,3-perfluoro-1,4-dioxanes of the formulae VII and VIII herein, are useful as solvents for highly fluorinated compounds, i.e., organic compounds which are mainly or exclusively substituted by fluorine, suc as hexafluoropropene and hexafluoropropene-epoxide along with their oligomers. These compounds are also useful as intermediates in various fields, for instance in pharmacy in the preparation of pharmaceuticals. Thus, for example 2,2,3,3-tetrafluoro-1,4-dioxane (=compound of formula I with X=Y=F) is a valuable intermediate in the preparation of hexafluoro-1,4-dioxane, the anaesthetic properties of which are known from U.S. Pat. No. 3,883,559. The preparation of said hexafluoro-1,4-dioxane via 2,2,3,3-tetrafluoro-1,4-dioxane can be illustrated by the following reaction scheme:

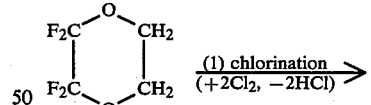

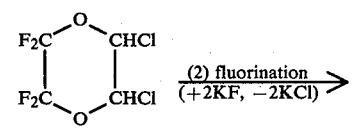

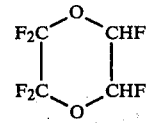

hexafluoro-1,4-dioxane

Step 1 of the reaction (=the chlorination) is performed like the chlorination of dioxane of 2,3-dichlorodioxane-1,4 described in Houben-Weyl, Vol. V/3, p. 610/1962), step 2 (=the fluorination) like the fluorination of 2,3- dichloro-dioxane-1,4 to 2,3-difluoro-dioxane-1,4 described in J. Org. Chem., Vol. 44, No. 13, pp. 2274–2277 esp. p. 2277 (1979).

The following examples illustrate the invention.

EXAMPLE 1

Into a dry 500 ml four-necked flash equipped with a thermometer, a reflux condenser, a KPG stirrer and a dropping funnel there are introduced 83.6 g (0.55 mol) of CsF in 250 ml of dry diglyme. 77 g (0.44 mol) of Cl-CH$_2$-CH$_2$-O-CF$_2$-COF are dropped into this mixture within about 30 min., the temperature reaching 44° C. Subsequently, the product is heated to 110°–120° C. for 8 hours, whilst the mixture becomes increasingly viscous. The cooled reaction mixture is subjected to steam distillation. The heavier phase hereby obtained is separated, dried over Na$_2$SO$_4$ and submitted to a fractionating distillation in a packed column. There are obtained 23 g (0.14 mol) of 2,2,3,3-tetrafluoro-1,4-dioxane.

Boiling point: 119°–121° C./750 mm.
Yield: 32.7% of the theory.

| | MW: | 160 | S.F.: C$_4$H$_4$F$_4$O$_2$ | |
|---|---|---|---|---|
| (structure) | Calc: | C 30.01 | H 2.52 | F 47.48 |
| | Found: | C 30.05 | H 2.50 | F 47.35 |

EXAMPLE 2

Into a 500 ml flask equipped with a usual stirrer, a reflux condenser, a thermometer and a dropping funnel and which has been annealed under nitrogen, there are introduced 31 g (0.2 mol) of CsF in 200 ml of dry diglyme. Within 90 minutes there are dropped in 45 g (0.2 mol) of Cl—CH$_2$—CH$_2$—O—CF(CF$_3$)—COF at 26°–29° C. Subsequently, the reaction mixture is heated to 120° C. whilst stirring and maintained for about 10 hours at this temperature. 35 g of an organic product are separated from the reaction mixture by steam distillation. The product contains 11 g (0.53 mol) of 2,3,3-trifluoro-2-trifluoromethyl-1,4-dioxane.

Boiling point: 74.5°–76.5° C./100 mm.
Yield: 26% of the theory.

| | MW: | 210 | S.F.: C$_5$H$_4$F$_6$O$_2$ | |
|---|---|---|---|---|
| (structure) | Calc: | C 28.57 | H 1.90 | F 54.28 |
| | Found: | C 29.00 | H 2.10 | F 53.00 |

EXAMPLE 3

Into an annealed 1-liter flask equipped with a usual stirrer, a reflux condenser, a thermometer and a gas inlet there are introduced 64 g (1.1 mol) of KF and 500 ml of dry diglyme. To this mixture there are added 47 g (0.5 mol) of oxalkylfluoride under ice cooling. Subsequently, the gas inlet is removed and 109 g (0.5 mol) of glycoldimesylate are added. The product is heated to 85° C. during about 24 hours and maintained at this temperature for 8 hours. In the subsequent steam distillation there are obtained 14 g of organic phase, which contain 8 g of 2,2,3,3-tetrafluoro-1,4-dioxane.

Yield: 10% of the theory.

EXAMPLE 4

The batch and reaction sequence is as in Example 3. There are added, however, a further 1.5 g (4.2 mmols) of the so-called crown ether dibenzo-18-crown-6; the latter compound is 2,3,11,12-dibenzo-1,4,7,10,13,16-hexaoxacyclooctadeca-2,11-diene of the formula:

(structure)

Yield: 8.8 g of 2,2,3,3-tetrafluoro-1,4-dioxane ≙ 11% of the theory.

EXAMPLE 5

The batch and reaction sequence is as in Example 3. There are added, however a further 7.5 g (0.05 mol) of CsF. Yield: 11.4 of 2,2,3,3-tetrafluoro-1,4-dioxane ≙ 14% of the theory.

EXAMPLE 6

Into a dry 500 ml flask equipped with a usual stirrer, a reflux condenser, a thermometer and a dropping funnel there are introduced 200 ml of tetraglyme and 95 g (0.625 mol) of caesium fluoride. Then 57 g (0.294 mol) of hexafluorodiacetyl are added drop by drop under ice cooling. The dropping funnel is subsequently removed and 80 g (0.37 mol) of glycaldimesylate are added. Subsequently, the product is stirred for 14 hours at 100°–105° C. 45 g of organic product are separated from the reaction mixture by steam distillation. Distillation gives 35 g (46% yield) of 2,3-bis-trifluoromethyl-2,3-difluoro-1,4-dioxane.

C$_6$H$_4$F$_8$O$_2$: Calc.: C, 27.71; H, 1.55; F, 58.44.
MW 260: Found: C, 27.75; H, 1.50; F, 57.95.
KP$_{100}$ 75°–90° C. (mixture of diastereomers).

What is claimed is:

1. A process for the manufacture of a 2,3-perfluoro-1,4-dioxane of the formula (structure)

wherein each of X and Y independently of the other is F or CF$_3$, which comprises reacting a carbonyl compound of the formula (structure)

wherein

X has the same meaning as above,

Y' is F, CF₃ or Cl, and

Z is Cl, OSO₂CH₃ or OSO₂C₆H₄—CH₃(-p) with at least one alkali metal fluoride, ammonium fluoride or combination thereof in an amount of at least about 1 mol of fluoride or combination of fluorides/mol of carbonyl compound if Y' is F or CF₃ or of at least about 2 mols of fluoride or combination of fluorides/mol of carbonyl compound if Y' is Cl, at a temperature of from about 20 to about 200° C. and normal or elevated pressure in an aprotic polar solvent for a time of from about 5 to 35 hours.

2. A process according to claim 1, wherein in the carbonyl compound Z is OSO₂CH₃ or OSO₂C₆H₄—CH₃(-p) and said compound is manufactured in situ by reaction of a fluorocarbonyl compound of the formula

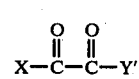

with an ethane derivative of the formula

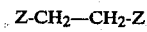

X being F or CF₃, Y' being F, CF₃ or Cl and Z being OSO₂CH₃ or OSO₂C₆H₄—CH₃(-p) and with at least one alkali metal fluoride, ammonium fluoride or combination thereof.

3. A process according to claim 1 or 2, which comprises reacting the carbonyl compound with KF, CsF or a combination thereof.

4. A process according to claim 1 or 2, wherein said at least one alkali metal fluoride, the ammonium fluoride or the combination thereof are employed in an excess of about 5 to 50%.

5. A process according to claim 1 or 2, wherein the reaction is carried out at a temperature of from about 50° to 160° C.

6. A process according to claim 5, wherein the reaction is carried out at a temperature of from about 60° to 130° C.

* * * * *